(12) United States Patent
Hoshino et al.

(10) Patent No.: US 8,648,194 B2
(45) Date of Patent: Feb. 11, 2014

(54) COMPOUNDS HAVING PHENANTHROLINE STRUCTURE

(75) Inventors: Mikio Hoshino, Tsurugashima (JP); Toshisada Yano, Kobe (JP)

(73) Assignee: B.R.A.H.M.S GmbH, Hennigsdorf (DE)

( * ) Notice: Subject to any disclaimer, the term of this patent is extended or adjusted under 35 U.S.C. 154(b) by 0 days.

(21) Appl. No.: 13/395,906

(22) PCT Filed: Sep. 13, 2010

(86) PCT No.: PCT/JP2010/005588
§ 371 (c)(1),
(2), (4) Date: May 23, 2012

(87) PCT Pub. No.: WO2011/030566
PCT Pub. Date: Mar. 17, 2011

(65) Prior Publication Data

US 2012/0238748 A1    Sep. 20, 2012

Related U.S. Application Data

(60) Provisional application No. 61/242,213, filed on Sep. 14, 2009.

(30) Foreign Application Priority Data

Sep. 14, 2009  (JP) .................................. 2009-212421

(51) Int. Cl.
*C07D 471/04*  (2006.01)

(52) U.S. Cl.
USPC .......................................................... 546/88

(58) Field of Classification Search
USPC .......................................................... 546/88
See application file for complete search history.

(56) References Cited

U.S. PATENT DOCUMENTS

| | | | |
|---|---|---|---|
| 5,424,381 A | 6/1995 | Yamamoto et al. | |
| 2006/0097227 A1 | 5/2006 | Okajima et al. | |
| 2009/0218940 A1 | 9/2009 | Okajima et al. | |
| 2012/0238748 A1 | 9/2012 | Hoshino et al. | |

FOREIGN PATENT DOCUMENTS

| | | |
|---|---|---|
| JP | 6-279572 | 10/1994 |
| WO | WO 2004/026870 A1 | 4/2004 |
| WO | WO 2011/030566 A1 | 3/2011 |

OTHER PUBLICATIONS

International Search Report and Written Opinion issued May 31, 2012 in PCT/JP2012/001707.
International Search Report issued Nov. 8, 2010 in PCT/JP2010/005588.
Theodora W. Greene, et al., "Protective Groups in Organic Synthesis", Second Edition, 1931, 490 pages.
J.I. G. Codagan, et al., "Dictionary of Organic Compounds", Sixth Edition, Published by Chapman and Hall, London, UK, vol. 5, M-0-00455-P-0-02796, 1996, 3 pages.
Dai-Yuki Kagaku, (Huge-Organic Chemistry), Fukusokanshiki Kagobutu (Heterocyclic Compound) III, vol. 16, Asakura Publishing Co., Ltd., Apr. 1964, supervised by Munio Kotake, pp. 356-363 (with whole English translation).
S. Ogawa, et al., J. Chem. Soc., Perkin Translation I, 1974, pp. 976-978.
Jeremy K. Klosterman, et al., "Synthesis of Aryl-Substituted 2-pyridyl-1, 10—phenanthrolines; a series of Oriented Terpyridine Analogues", Organic & Bimolecular Chemistry, Aug. 7, 2008, XP002606398, vol. 6, No. 15, ISSN:1477-0520, pp. 2755-2764.
Jon C. Loren, et al., "Synthesis and Fluorescence Properties of Manisyl-Substituted Terpyridine, Bipyridine, and Phenanthroline", Angewandte Chemie International Edition, XP002606399, vol. 40, No. 4. 2001, pp. 754-757.

*Primary Examiner* — Andrew D Kosar
*Assistant Examiner* — John S Kenyon
(74) *Attorney, Agent, or Firm* — Oblon, Spivak, McClelland, Maier & Neustadt, L.L.P.

(57) ABSTRACT

The present invention provides a novel compound having a phenanthroline structure represented by formula (I) or a salt thereof:

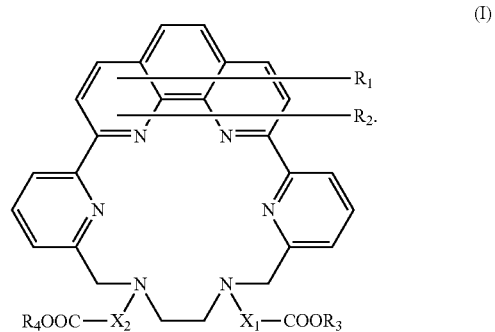

3 Claims, No Drawings

COMPOUNDS HAVING PHENANTHROLINE STRUCTURE

TECHNICAL FIELD

The present invention relates to a novel compound having a phenanthroline structure or a salt thereof.

BACKGROUND ART

Recently, functions of metal complex compounds such as photoreactive functions, electron-transfer functions, and physiologically active functions have been attracting attention, and a number of researches are being conducted by utilizing such functions. Further, researches on ligands that bind to coordination metal have also been conducted. As a representative ligand, a unidentate ligand such as ammonia, pyridine, and a cyanide ion, a bidentate ligand such as ethylenediamine, bipyridine, and glycinato, and a multidentate ligand having a coordination number of three or more such as ethylenediaminetetraacetic acid are known.

Bipyridine, which is a representative bidentate ligand, has a chelate ligand structure and a function of coordinating with a metal element. However, owing to poor solubility of bipyridine complexes in organic solvents, there has been a problem that the utility range of such a complex is extremely limited.

Patent Literature 1 discloses a compound in which a long-chain alkyl group such as a hexyl group, a pentyl group, an octyl group, and a decyl group is introduced into polybipyridine.

CITATION LIST

Patent Literature

[PTL 1] Japanese Patent Laid-Open No. 6-279572

SUMMARY OF INVENTION

Technical Problem

Creation of a compound that is further improved compared to an existing compound is demanded.

Solution to Problem

In order to solve the aforementioned problem, the present inventors conducted intensive studies. As a result, they have found a novel compound having a phenan-throline structure, thereby completing the present invention.

That is, the present inventions are as follows.

[1] A compound having a phenanthroline structure represented by the following formula (I) or a salt thereof:

Formula (I):

[Chem. 1]

wherein, $R_1$ and $R_2$ are the same as or different from each other and each independently represents (1) a hydrogen atom, (2) a halogen atom, (3) a hydroxyl group, (4) a cyano group, (5) a nitro group, (6) an amino group, (7) a $C_{1-6}$ alkyl group, (8) a $C_{3-8}$ cycloalkyl group, (9) a $C_{2-6}$ alkenyl group, (10) a $C_{2-6}$ alkynyl group, (11) a $C_{1-6}$ alkoxy group, (12) a $C_{3-8}$ cycloalkoxy group, (13) a $C_{2-6}$ alkenyloxy group, (14) a $C_{2-6}$ alkynyloxy group, (15) a $C_{1-6}$ alkylthio group, (16) a $C_{3-8}$ cycloalkylthio group, (17) a $C_{2-6}$ alkenylthio group, (18) a $C_{2-6}$ alkynylthio group, (19) a $C_{1-6}$ alkylcarbonyloxy group, (20) a formyl group, (21) a $C_{1-6}$ alkylcarbonyl group, (22) a $C_{1-6}$ alkylamino group, (23) a di-$C_{1-6}$ alkylamino group, (24) a $C_{1-6}$ alkylsulfinyl group, (25) a $C_{1-6}$ alkylsulfonyl group, (26) a $C_{3-8}$ cycloalkylsulfinyl group, (27) a $C_{3-8}$ cycloalkylsulfonyl group, (28) a carboxyl group, (29) a $C_{1-6}$ alkyloxycarbonyl group, (30) a $C_{6-14}$ aryl group, or (31) a $C_{7-20}$ aralkyl group;

$R_3$ and $R_4$ are the same as or different from each other and each independently represents (1) a hydrogen atom, (2) a $C_{1-6}$ alkyl group, (3) a $C_{3-8}$ cycloalkyl group, (4) a $C_{2-6}$ alkenyl group, (5) a $C_{2-6}$ alkynyl group, (6) a $C_{6-14}$ aryl group, or (7) a $C_{7-20}$ aralkyl group; and $X_1$ and $X_2$ are the same as or different from each other and each independently represents the following structure:

[Chem. 2]

$$—(CH_2)_m— \quad \text{or} \quad —(CH_2)_{m-1}CH— \\ | \\ COOR_5$$

wherein, m represents an integer of 1 to 6; and $R_5$ represents (1) a hydrogen atom, (2) a $C_{1-6}$ alkyl group, (3) a $C_{3-8}$ cycloalkyl group, (4) a $C_{2-6}$ alkenyl group, (5) a $C_{2-6}$ alkynyl group, (6) a $C_{6-14}$ aryl group, or (7) a $C_{7-20}$ aralkyl group.

[2] The compound or the salt thereof according to [1], wherein each of $R_3$ and $R_4$ represents a hydrogen atom.

[3] A compound having a phenanthroline structure represented by the following formula (I') or a salt thereof:

Formula (I'):

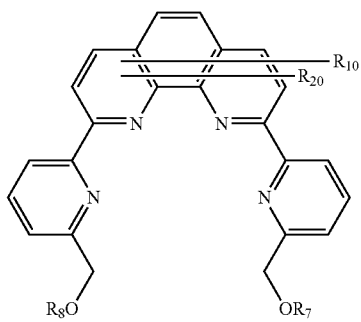

wherein, $R_{10}$ and $R_{20}$ are the same as or different from each other and each independently represents (1) a hydrogen atom, (2) a halogen atom, (3) a hydroxyl group, (4) a cyano group, (5) a nitro group, (6) an amino group, (7) a $C_{1-6}$ alkyl group, (8) a $C_{3-8}$ cycloalkyl group, (9) a $C_{2-6}$ alkenyl group, (10) a $C_{2-6}$ alkynyl group, (11) a $C_{1-6}$ alkoxy group, (12) a $C_{3-8}$ cycloalkoxy group, (13) a $C_{2-6}$ alkenyloxy group, (14) a $C_{2-6}$ alkynyloxy group, (15) a $C_{1-6}$ alkylthio group, (16) a $C_{3-8}$ cycloalkylthio group, (17) a $C_{2-6}$ alkenylthio group, (18) a $C_{2-6}$ alkynylthio group, (19) a $C_{1-6}$ alkylcarbonyloxy group, (20) a formyl group, (21) a $C_{1-6}$ alkylcarbonyl group, (22) a $C_{1-6}$ alkylamino group, (23) a di-$C_{1-6}$ alkylamino group, (24) a $C_{1-6}$ alkylsulfinyl group, (25) a $C_{1-6}$ alkylsulfonyl group, (26) a $C_{3-8}$ cycloalkylsulfinyl group, (27) a $C_{3-8}$ cycloalkylsulfonyl group, (28) a carboxyl group, (29) a $C_{1-6}$ alkyloxycarbonyl group, (30) a $C_{6-14}$ aryl group, or (31) a $C_{7-20}$ aralkyl group, or a group that can be converted to the group (1) to (31); and $R_7$ and $R_8$ are the same as or different from each other and each independently represents a hydrogen atom or a protective group.

DESCRIPTION OF EMBODIMENTS

The novel compound having a phenanthroline structure or a salt thereof of the present invention is a compound represented by the following formula (I) or a salt thereof:

Formula (I):

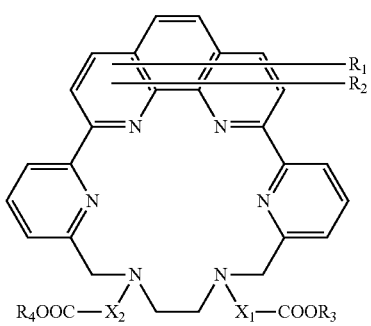

wherein, $R_1$ and $R_2$ are the same as or different from each other and each independently represents (1) a hydrogen atom, (2) a halogen atom, (3) a hydroxyl group, (4) a cyano group, (5) a nitro group, (6) an amino group, (7) a $C_{1-6}$ alkyl group, (8) a $C_{3-8}$ cycloalkyl group, (9) a $C_{2-6}$ alkenyl group, (10) a $C_{2-6}$ alkynyl group, (11) a $C_{1-6}$ alkoxy group, (12) a $C_{3-8}$ cycloalkoxy group, (13) a $C_{2-6}$ alkenyloxy group, (14) a $C_{2-6}$ alkynyloxy group, (15) a $C_{1-6}$ alkylthio group, (16) a $C_{3-8}$ cycloalkylthio group, (17) a $C_{2-6}$ alkenylthio group, (18) a $C_{2-6}$ alkynylthio group, (19) a $C_{1-6}$ alkylcarbonyloxy group, (20) a formyl group, (21) a $C_{1-6}$ alkylcarbonyl group, (22) a $C_{1-6}$ alkylamino group, (23) a di-$C_{1-6}$ alkylamino group, (24) a $C_{1-6}$ alkylsulfinyl group, (25) a $C_{1-6}$ alkylsulfonyl group, (26) a $C_{3-8}$ cycloalkylsulfinyl group, (27) a $C_{3-8}$ cycloalkylsulfonyl group, (28) a carboxyl group, (29) a $C_{1-6}$ alkyloxycarbonyl group, (30) a $C_{6-14}$ aryl group, or (31) a $C_{7-20}$ aralkyl group;

$R_3$ and $R_4$ are the same as or different from each other and each independently represents (1) a hydrogen atom, (2) a $C_{1-6}$ alkyl group, (3) a $C_{3-8}$ cycloalkyl group, (4) a $C_{2-6}$ alkenyl group, (5) a $C_{2-6}$ alkynyl group, (6) a $C_{6-14}$ aryl group, or (7) a $C_{7-20}$ aralkyl group; and $X_1$ and $X_2$ are the same as or different from each other and each independently represents the following structure:

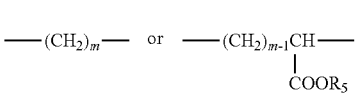

wherein, m represents an integer of 1 to 6; and $R_5$ represents (1) a hydrogen atom, (2) a $C_{1-6}$ alkyl group, (3) a $C_{3-8}$ cycloalkyl group, (4) a $C_{2-6}$ alkenyl group, (5) a $C_{2-6}$ alkynyl group, (6) a $C_{6-14}$ aryl group, or (7) a $C_{7-20}$ aralkyl group.

The terms used in the present specification will be described.

The term "halogen atom" refers to a fluorine atom, a chlorine atom, a bromine atom, an iodine atom, and the like. Among them, a chlorine atom, a bromine atom, and an iodine atom are preferable, and a chlorine atom and a bromine atom are more preferable.

The term "$C_{1-6}$ alkyl group" refers to a linear-chain or branched-chain aliphatic hydrocarbon group containing 1 to 6 carbons. Specific examples thereof include a methyl group, an ethyl group, a propyl group, an isopropyl group, a butyl group, a sec-butyl group, a tert-butyl group, a pentyl group, an isopentyl group, and a hexyl group. Among them, a methyl group, an ethyl group, a propyl group, and a tert-butyl group are preferable, and a methyl group and an ethyl group are more preferable.

The term "$C_{3-8}$ cycloalkyl group" refers to a cyclic aliphatic hydrocarbon group containing 3 to 8 carbons. Specific examples thereof include a cyclopropyl group, a cyclobutyl group, a cyclopentyl group, a cyclohexyl group, and a cyclooctyl group. Among them, a cyclopropyl group, a cyclobutyl group, a cyclopentyl group, and a cyclohexyl group are preferable, and a cyclopropyl group and a cyclobutyl group are more preferable.

The term "$C_{2-6}$ alkenyl group" refers to a linear-chain or branched-chain aliphatic hydrocarbon group containing 2 to 6 carbons and having one or two double bonds.

Specific examples thereof include an ethenyl group, a 2-propenyl group, a 1-propenyl group, a 1-methyl vinyl group, a 1-butenyl group, a 2-butenyl group, a 3-butenyl group, a 1,3-pentadienyl group, a 1,4-hexadienyl group, a 5-pentenyl group, and a 6-hexenyl group. Among them, an ethenyl group, a 2-propenyl group, a 1-propenyl group, and a 1-methyl vinyl group are preferable, and an ethenyl group and a 1-propenyl group are more preferable.

The term "$C_{2-6}$ alkynyl group" refers to a linear-chain or a branched-chain aliphatic hydrocarbon group containing 2 to 6 carbons and having one or two triple bonds. Specific examples thereof include an ethynyl group, a 1-propynyl group, a 2-propynyl group, a butynyl group, a 1,3-pentanediynyl group, a 1,4-hexadiynyl group, a pentynyl group, and a hexynyl group. Among them, an ethynyl group, a 1-propynyl group, a 2-propynyl group, and a butynyl group are preferable, and an ethynyl group and a 2-propynyl group are more preferable.

The term "$C_{1-6}$ alkoxy group" refers to a group with an oxygen atom to which a $C_{1-6}$ alkyl group is bonded. Specific examples thereof include a methoxy group, an ethoxy group, a propoxy group, an isopropoxy group, a butoxy group, a sec-butoxy group, a tert-butoxy group, a pentyloxy group, an isopentyloxy group, and a hexyloxy group. Among them, a methoxy group, an ethoxy group, a propoxy group, and a tert-butoxy group are preferable, and a methoxy group and an ethoxy group are more preferable.

The term "$C_{3-8}$ cycloalkoxy group" refers to a group with an oxygen atom to which a $C_{3-8}$ cycloalkyl group is bonded. Specific examples thereof include a cyclopropoxy group, a cyclobutoxy group, a cyclopentyloxy group, a cyclohexyloxy group, and a cyclooctyloxy group. Among them, a cyclopropoxy group, a cyclobutoxy group, a cyclopentyloxy group, and a cyclohexyloxy group are preferable, and a cyclopropoxy group and a cyclobutoxy group are more preferable.

The term "$C_{2-6}$ alkenyloxy group" refers to a group with an oxygen atom to which a $C_{2-6}$ alkenyl group is bonded. Specific examples thereof include an ethenyloxy group, a 2-propenyloxy group, a 1-propenyloxy group, a 1-methylvinyloxy group, a 1-butenyloxy group, a 2-butenyloxy group, a 3-butenyloxy group, a 1,3-pentadienyloxy group, a 1,4-hexadienyloxy group, a 5-pentenyloxy group, and a 6-hexenyloxy group. Among them, an ethenyloxy group, a 2-propenyloxy group, a 1-propenyloxy group, and a 1-methylvinyloxy group are preferable, and an ethenyloxy group and a 1-propenyloxy group are more preferable.

The term "$C_{2-6}$ alkynyloxy group" refers to a group with an oxygen atom to which a $C_{2-6}$ alkynyl group is bonded. Specific examples thereof include an ethynyloxy group, a 1-propynyloxy group, a 2-propynyloxy group, a butynyloxy group, a 1,3-pentanediynyloxy group, a 1,4-hexadiynyloxy group, a pentynyloxy group, and a hexynyloxy group. Among them, an ethynyloxy group, a 1-propynyloxy group, a 2-propynyloxy group, and a butynyloxy group are preferable, and an ethynyloxy group and a 2-propynyloxy group are more preferable.

The term "$C_{1-6}$ alkylthio group" refers to a group with a sulfur atom to which a $C_{1-6}$ alkyl group is bonded. Specific examples thereof include a methylthio group, an ethylthio group, a propylthio group, an isopropylthio group, a butylthio group, a sec-butylthio group, a tert-butylthio group, a pentylthio group, an isopentylthio group, and a hexylthio group. Among them, a methylthio group, an ethylthio group, a propylthio group, and a tert-butylthio group are preferable, and a methylthio group and an ethylthio group are more preferable.

The term "$C_{3-8}$ cycloalkylthio group" refers to a group with a sulfur atom to which a $C_{3-8}$ cycloalkyl group is bonded. Specific examples thereof include a cyclopropylthio group, a cyclobutylthio group, a cyclopentylthio group, a cyclohexylthio group, and a cyclooctylthio group. Among them, a cyclopropylthio group, a cyclobutylthio group, a cyclopentylthio group, and a cyclohexylthio group are preferable, and a cyclo-propylthio group and a cyclobutylthio group are more preferable.

The term "$C_{2-6}$ alkenylthio group" refers to a group with a sulfur atom to which a $C_{2-6}$ alkenyl group is bonded. Specific examples thereof include an ethenylthio group, a 2-propenylthio group, a 1-propenylthio group, a 1-methylvinylthio group, a 1-butenylthio group, a 2-butenylthio group, a 3-butenylthio group, a 1,3-pentadienylthio group, a 1,4-hexadienylthio group, a 5-pentenylthio group, and a 6-hexenylthio group. Among them, an ethenylthio group, a 2-propenylthio group, a 1-propenylthio group, and a 1-methyl vinylthio group are preferable, and an ethenylthio group and a 1-propenylthio group are more preferable.

The term "$C_{2-6}$ alkynylthio group" refers to a group with a sulfur atom to which a $C_{2-6}$ alkynyl group is bonded. Specific examples thereof include an ethynylthio group, a 1-propynylthio group, a 2-propynylthio group, a butynylthio group, a 1,3-pentanediynylthio group, a 1,4-hexadiynylthio group, a pentynylthio group, and a hexynylthio group. Among them, an ethynylthio group, a 1-propynylthio group, a 2-propynylthio group, and a butynylthio group are preferable, and an ethynylthio group and a 2-propynylthio group are more preferable.

The term "$C_{1-6}$ alkylcarbonyloxy group" refers to a carbonyloxy group to which a $C_{1-6}$ alkyl group is bonded. Specific examples thereof include a methylcarbonyloxy group, an ethylcarbonyloxy group, a propylcarbonyloxy group, an isopropylcarbonyloxy group, a butylcarbonyloxy group, a sec-butylcarbonyloxy group, a tert-butylcarbonyloxy group, a pentylcarbonyloxy group, an isopentylcarbonyloxy group, and a hexylcarbonyloxy group. Among them, a methylcarbonyloxy group, an ethylcarbonyloxy group, a propylcarbonyloxy group, and a tert-butylcarbonyloxy group are preferable, and a methylcarbonyloxy group and an ethylcarbonyloxy group are more preferable.

The term "$C_{1-6}$ alkylcarbonyl group" refers to a carbonyl group to which a $C_{1-6}$ alkyl group is bonded. Specific examples thereof include a methylcarbonyl group, an ethylcarbonyl group, a propylcarbonyl group, an isopropylcarbonyl group, a butylcarbonyl group, a sec-butylcarbonyl group, a tert-butylcarbonyl group, a pentylcarbonyl group, an isopentylcarbonyl group, and a hexylcarbonyl group. Among them, a methyl-carbonyl group, an ethylcarbonyl group, a propylcarbonyl group, and a tert-butylcarbonyl group are preferable, and a methylcarbonyl group and an ethylcarbonyl group are more preferable.

The term "$C_{1-6}$ alkylamino group" refers to a group with a nitrogen atom to which a $C_{1-6}$ alkyl group is bonded. Specific examples thereof include an N-methylamino group, an N-ethylamino group, an N-propylamino group, an N-isopropylamino group, an N-butylamino group, an N-sec-butylamino group, an N-tert-butylamino group, an N-pentylamino group, an N-isopentylamino group, and an N-hexylamino group. Among them, an N-methylamino group, an N-ethylamino group, an N-propylamino group, and an N-tert-butylamino group are preferable, and an N-methylamino group and an N-ethylamino group are more preferable.

The term "di-$C_{1-6}$ alkylamino group" refers to a group with a nitrogen atom to which two $C_{1-6}$ alkyl groups are bonded. The two alkyl groups bonded to an amino group may be identical or different. Specific examples thereof include an N,N-dimethylamino group, an N-ethyl-N-methylamino group, an N,N-diethylamino group, an N,N-dipropylamino group, an N,N-diisopropylamino group, an N,N-dibutylamino group, an N,N-di-sec-butylamino group, an N,N-di-tert-butylamino group, an N,N-dipentylamino group, an N,N-diisopentylamino group, and an N,N-dihexylamino group. Among them, an N,N-dimethylamino group, N-ethyl-N-methylamino group, an N,N-diethylamino group, an N,N-dipropylamino group, and an N,N-di-tert-butylamino group are preferable, and an N,N-dimethylamino group, an N,N-diethylamino group, and an N-ethyl-N-methylamino group are more preferable.

The term "$C_{1-6}$ alkylsulfinyl group" refers to a sulfinyl group (—SO—) to which a $C_{1-6}$ alkyl group is bonded. Specific examples thereof include a methanesulfinyl group, an ethanesulfinyl group, a propanesulfinyl group, an isopropanesulfinyl group, a butane-sulfinyl group, a sec-butanesulfinyl group, a tert-butanesulfinyl group, a pentane-sulfinyl group, an isopentanesulfinyl group, and a hexanesulfinyl group. Among them, a methanesulfinyl group, an ethanesulfinyl group, a propanesulfinyl group, and a tert-butanesulfinyl group are preferable, and a methanesulfinyl group and an ethanesulfinyl group are more preferable.

The term "$C_{1-6}$ alkylsulfonyl group" refers to a sulfonyl group (—SO$_2$—) to which a $C_{1-6}$ alkyl group is bonded. Specific examples thereof include a methanesulfonyl group, an ethanesulfonyl group, a propanesulfonyl group, an isopropanesulfonyl group, a butane-sulfonyl group, a sec-butanesulfonyl group, a tert-butanesulfonyl group, a pentane-sulfonyl group, an isopentanesulfonyl group, and a hexanesulfonyl group. Among them, a methanesulfonyl group, an ethanesulfonyl group, a propanesulfonyl group, and a tert-butanesulfonyl group are preferable, and a methanesulfonyl group and an ethane-sulfonyl group are more preferable.

The term "$C_{3-8}$ cycloalkylsulfinyl group" refers to a sulfinyl group to which a $C_{3-8}$ cycloalkyl group is bonded. Specific examples thereof include a cyclopropanesulfinyl group, a cyclobutanesulfinyl group, a cyclopentanesulfinyl group, a cyclohexane-sulfinyl group, and a cyclooctanesulfinyl group. Among them, a cyclopropanesulfinyl group, a cyclobutanesulfinyl group, a cyclopentanesulfinyl group, and a cyclohexane-sulfinyl group are preferable, and a cyclopropanesulfinyl group and a cyclobutane-sulfinyl group are more preferable.

The term "$C_{3-8}$ cycloalkylsulfonyl group" refers to a sulfonyl group to which a $C_{3-8}$ cycloalkyl group is bonded. Specific examples thereof include a cyclopropanesulfonyl group, a cyclobutanesulfonyl group, a cyclopentanesulfonyl group, a cyclohexane-sulfonyl group, and a cyclooctanesulfonyl group. Among them, a cyclopropanesulfonyl group, a cyclobutanesulfonyl group, a cyclopentanesulfonyl group, and a cyclohexane-sulfonyl group are preferable, and a cyclopropanesulfonyl group and a cyclobutane-sulfinyl group are more preferable.

The term "$C_{1-6}$ alkyloxycarbonyl group" refers to a carboxyl group to which a $C_{1-6}$ alkyl group is bonded via an ester bond. Specific examples thereof include a methyloxycarbonyl group, an ethyloxycarbonyl group, a propyloxycarbonyl group, an iso-propyloxycarbonyl group, a butyloxycarbonyl group, a sec-butyloxycarbonyl group, a tert-butyloxycarbonyl group, a pentyloxycarbonyl group, an isopentyloxycarbonyl group, and a hexyloxycarbonyl group. Among them, a methyloxycarbonyl group, an ethyloxycarbonyl group, a propyloxycarbonyl group, and a tert-butyloxycarbonyl group are preferable, and a methyloxycarbonyl group and an ethyloxycarbonyl group are more preferable.

The term "$C_{6-14}$ aryl group" refers to an aromatic hydrocarbon group containing 6 to 14 carbons. Specific examples thereof include a phenyl group, a naphthyl group, and an anthranyl group. Among them, a phenyl group and a naphthyl group are preferable, and a phenyl group is more preferable.

The term "$C_{7-20}$ aralkyl group" refers to a $C_{1-6}$, preferably $C_{1-4}$ alkyl group to which a $C_{6-14}$, preferably $C_{6-10}$ aryl group is bonded. It is preferably a $C_{7-14}$ aralkyl group. Specific examples thereof include a benzyl group, a phenethyl group, or a naphtylmethyl group.

In the present specification, even when a group is described as a $C_{1-6}$ alkyl as in "$C_{1-6}$ alkylcarbonyloxy group" and the like, the $C_{1-6}$ alkyl may also be a $C_{3-8}$ cycloalkyl, a $C_{2-6}$ alkenyl group, a $C_{2-6}$ alkynyl group, or a $C_{3-8}$ cycloalkyl $C_{1-2}$ alkyl.

In the formula (I), $R_1$ and $R_2$ are the same as or different from each other and each independently represents (1) a hydrogen atom, (2) a halogen atom, (3) a hydroxyl group, (4) a cyano group, (5) a nitro group, (6) an amino group, (7) a $C_{1-6}$ alkyl group, (8) a $C_{3-8}$ cycloalkyl group, (9) a $C_{2-6}$ alkenyl group, (10) a $C_{2-6}$ alkynyl group, (11) a $C_{1-6}$ alkoxy group, (12) a $C_{3-8}$ cycloalkoxy group, (13) a $C_{2-6}$ alkenyloxy group, (14) a $C_{2-6}$ alkynyloxy group, (15) a $C_{1-6}$ alkylthio group, (16) a $C_{3-8}$ cycloalkylthio group, (17) a $C_{2-6}$ alkenylthio group, (18) a $C_{2-6}$ alkynylthio group, (19) a $C_{1-6}$ alkylcarbonyloxy group, (20) a formyl group, (21) a $C_{1-6}$ alkylcarbonyl group, (22) a $C_{1-6}$ alkylamino group, (23) a di-$C_{1-6}$ alkylamino group, (24) a $C_{1-6}$ alkylsulfinyl group, (25) a $C_{1-6}$ alkylsulfonyl group, (26) a $C_{3-8}$ cycloalkylsulfinyl group, (27) a $C_{3-8}$ cycloalkylsulfonyl group, (28) a carboxyl group, (29) a $C_{1-6}$ alkyloxycarbonyl group, (30) a $C_{6-14}$ aryl group, or (31) a $C_{7-20}$ aralkyl group. Among them, (1) a hydrogen atom, (3) a hydroxyl group, (5) a nitro group, (6) an amino group, (7) a $C_{1-6}$ alkyl group, (11) a $C_{1-6}$ alkoxy group, (12) a $C_{3-8}$ cycloalkoxy group, (22) a $C_{1-6}$ alkylamino group, (23) a di-$C_{1-6}$ alkylamino group, or (29) a $C_{1-6}$ alkyloxycarbonyl group is preferable, and (1) a hydrogen atom, (5) a nitro group, (6) an amino group, (7) a $C_{1-6}$ alkyl group, (22) a $C_{1-6}$ alkylamino group, or (23) a di-$C_{1-6}$ alkylamino group, or (29) a $C_{1-6}$ alkyloxycarbonyl group is more preferable.

In the formula (I), $R_3$ and $R_4$ are the same as or different from each other and each independently represents (1) a hydrogen atom, (2) a $C_{1-6}$ alkyl group, (3) a $C_{3-8}$ cycloalkyl group, (4) a $C_{2-6}$ alkenyl group, (5) a $C_{2-6}$ alkynyl group, (6) a $C_{6-14}$ aryl group, or (7) a $C_{7-20}$ aralkyl group. Among them, (1) a hydrogen atom, (2) a $C_{1-6}$ alkyl group, or (7) a $C_{7-20}$ aralkyl group is preferable, and (1) a hydrogen atom is more preferable.

In the formula (I), $X_1$ and $X_2$ are the same as or different from each other and each independently represents the following structure:

[Chem. 6]

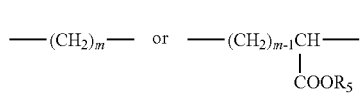

In the above structure, m represents an integer of 1 to 6, preferably an integer of 1 or 2.

In the above structure, $R_5$ represents (1) a hydrogen atom, (2) a $C_{1-6}$ alkyl group, (3) a $C_{3-8}$ cycloalkyl group, (4) a $C_{2-6}$ alkenyl group, (5) a $C_{2-6}$ alkynyl group, (6) a $C_{6-14}$ aryl group, or (7) a $C_{7-20}$ aralkyl group. Among them, (1) a hydrogen atom is preferable.

The salt of the compound represented by the formula (I) refers to, for example, a base addition salt such as an alkali metal salt such as a sodium salt and a potassium salt, and an alkaline earth metal salt such as a calcium salt and a magnesium salt, and, for example, an acid addition salt such as a hydrochloride and a sulfate. Examples thereof include a salt formed with a hydroxyl group (specifically, a phenolic hydroxyl group and the like) or a carboxyl group (—COOH), or a base (specifically, an NH group and the like) present in the compound represented by the formula (I).

The salt of the compound represented by the formula (I) is producible by carrying out an ordinary salt formation reaction.

Among those compounds represented by the formula (I), a preferable compound is specifically 2,5-bis-carboxymethyl-2,5-diazo[6]-(5',5')-cyclo-2,9-di-(2'-pyridyl)-1,10-phenanthrolin ophane.

The production method of the compound represented by the formula (I) will be described.

As shown in the following scheme (I), the compound represented by the formula (I) is producible by reacting a compound represented by the formula (II) with a compound represented by the formula (III).

Further, the compound represented by the formula (I) is producible by, after reacting a compound represented by the formula (II) with a compound represented by the formula (III), appropriately introducing and/or converting a desired substituent by an ordinary method.

Scheme (I):

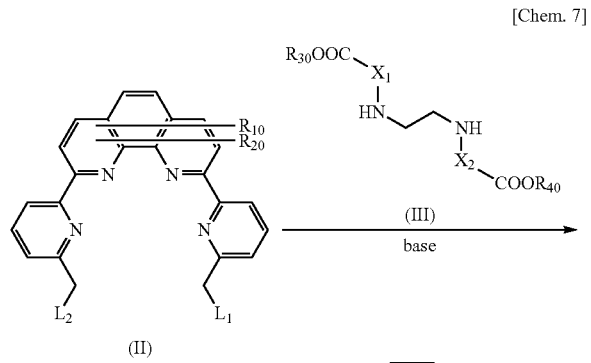

$R_1$ to $R_4$ as well as $X_1$ and $X_2$ in the scheme (I) represent the same groups as described above, and $R_{10}$ and $R_{20}$ are the same as or different from each other and each independently may be the same groups as $R_1$ and $R_2$, or groups that can be converted to groups represented by $R_1$ and $R_2$ such as those that are protected by protective groups.

$R_{30}$ and $R_{40}$ are the same as or different from each other and each independently may be the same groups as $R_3$ and $R_4$, or groups that can be converted to groups represented by $R_3$ and $R_4$ such as those that are protected by protective groups.

$L_1$ and $L_2$ are the same as or different from each other and each independently represents a leaving group.

Reactions in the scheme (I) can be carried out by reacting a compound represented by the formula (II) with a compound represented by the formula (III) in an inert solvent in the presence of a base.

The compound represented by the formula (III) is preferably used in an amount of one to three equivalents, more preferable one to 1.5 equivalents relative to the compound represented by the formula (II).

The inert solvent used in the reaction is not particularly limited, as long as it allows the reaction of the compound represented by the formula (II) and the compound represented by the formula (III) to smoothly proceed. Examples thereof include ethyl methyl ketone, acetonitrile, acetone, dimethylformamide, and dimethylacetamide. Among them, ethyl methyl ketone, acetonitrile, and acetone are preferable, and ethyl methyl ketone is more preferable.

The base is preferably used in an amount of one to 10 equivalents, more preferable one to five equivalents relative to the compound represented by the formula (II).

Generally, the reaction is preferably carried out under non-aqueous conditions. The reaction is carried out preferably at from room temperature to the boiling point of the solvent, more preferably while heating under reflux. The reaction is completed in 10 hours to 10 days.

The compound represented by the formula (I) may be a compound directly produced by reacting the compound represented by the formula (II) with the compound represented by the formula (III). As shown in the following scheme (II), after producing a compound represented by the formula (I-1), the compound can be converted to the desired compound represented by the formula (I) appropriately in accordance with an ordinary method.

Scheme (II):

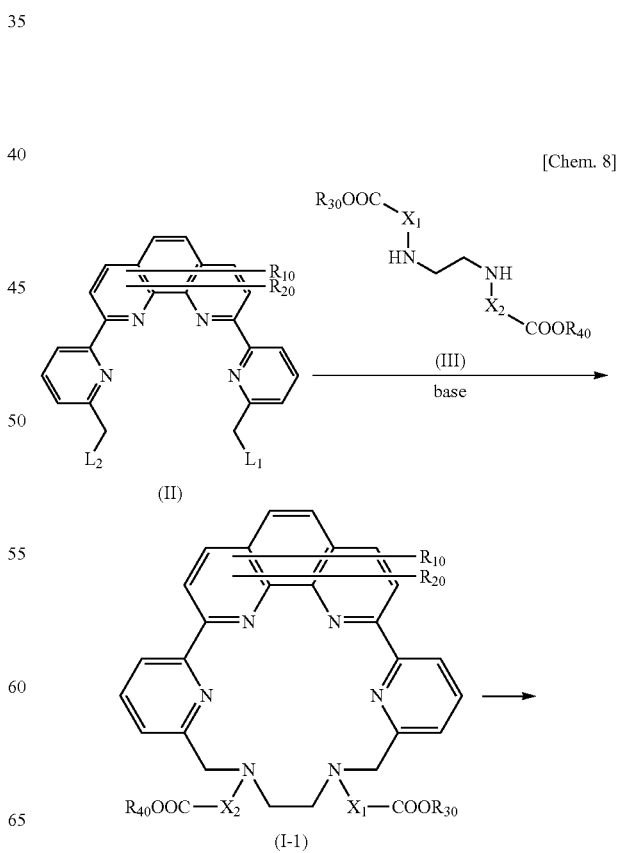

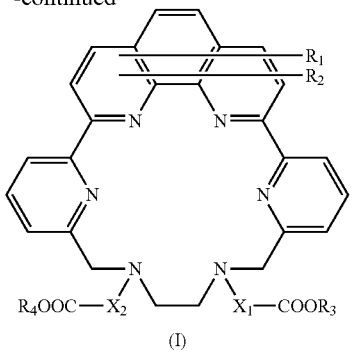

(I)

The compound represented by the formula (III) may be a well-known or a commercially-available compound, or a compound that is producible in accordance with a known method or that can have desired $R_3$ and $R_4$ introduced thereinto or removed therefrom. $R_{30}$ and $R_{40}$ may be a protective group of a carboxyl group, and in the compound represented by the formula (I-1), $R_{30}$ and $R_{40}$ are deprotected to obtain a carboxyl group, and then $R_3$ and $R_4$ may be introduced.

In the production of the compound represented by the formula (I), $R_{30}$ and $R_{40}$ present in the compound represented by the formula (III) used in the reaction may be a protective group of a carboxyl group. Examples thereof include a lower alkyl group such as a methyl group, an ethyl group, a propyl group, an isopropyl group, and a tert-butyl group; a halo-substituted lower alkyl group such as a 2,2,2-trichloroethyl group and a 2,2,2-trifluoroethyl group; a lower alkanoyloxyalkyl group such as an acetoxymethyl group, a propionyloxymethyl group, a pivaloyloxymethyl group, a 1-acetoxyethyl group, and a 1-propionyloxyethyl group; a lower alkoxycarbonyloxyalkyl group such as 1-(methoxycarbonyloxy)ethyl group, a 1-(ethoxycarbonyloxy)ethyl group, a 1-(isopropoxycarbonyloxy)ethyl group; a lower alkenyl group such as a 2-propenyl group, a 2-chloro-2-propenyl group, a 3-methoxycarbonyl-2-propenyl group, a 2-methyl-2-propenyl group, a 2-butenyl group, and a cinnamyl group; an aralkyl group such as a benzyl group, a p-methoxybenzyl group, a 3,4-dimethoxybenzyl group, an o-nitrobenzyl group, a p-nitrobenzyl group, a benzhydryl group, and a bis(p-methoxyphenyl)methyl group; a (5-substituted-2-oxo-1,3-dioxol-4-yl)methyl group such as a (5-methyl-2-oxo-1,3-dioxol-4-yl)methyl group; a lower alkylsilyl group such as a trimethylsilyl group and a tert-butyldimethylsilyl group, an indanyl group, a phthalidyl group, and a methoxyethyl group. Removal of the protective group of a carboxyl group differs depending on the kind of the protective group and the stability of the compound. In accordance with the method described in "Protective Groups In Organic Synthesis, Second Edition by T. W. Greene and P. G. M. Wuts, John Wiley&Sons, Inc." or a method according to the above method, removal of the protective group, but is not particularly limited to, can be carried out by, for example, a solvolysis reaction using an acid or a base, chemical reduction using a hydrogenated metal complex and the like, and catalytic reduction using a palladium carbon catalyst, a raney nickel catalyst, and the like. Examples of the base include an alkali metal hydroxide such as sodium hydroxide and potassium hydroxide.

The solvent to be used in the present process, but is not particularly limited to, is preferably an inert solvent that does not easily react with starting materials. Examples thereof include water, alcohols such as methanol, ethanol, isopropanol, and tert-butanol, ethers such as tetrahydrofuran, diethyl ether, diisopropyl ether, dioxane, and dimethoxyethane, halogenated hydrocarbons such as methylene chloride, chloroform, carbon tetrachloride, and 1,2-dichloroethane, hydrocarbons such as hexane, benzene, and toluene, ketones such as acetone and methyl ethyl ketone, nitriles such as acetonitrile, amides such as N,N-dimethylformamide, N,N-dimethylacetamide, N-methyl-2-pyrrolidone, and hexamethylphosphorylamide, and sulfoxides such as dimethyl sulfoxide, or a mixture of these solvents. Among them, alcohols such as methanol and ethers such as tetrahydrofuran and dimethoxyethane are preferable. The reaction temperature is preferably 0 to 100° C., more preferably 10 to 30° C. The reaction time is preferably 1 to 20 hours, more preferably 3 to 10 hours.

In the production of the compound represented by the formula (I), functional groups present in the compound represented by the formula (II) used in the reaction may be appropriately protected. As the protective group used in the reaction, one that is normally used as a protective group of, for example, a hydroxyl group, a carboxyl group, a carbonyl group, and an amino group can be employed. Examples thereof include, but are not particularly limited to, protective groups that are described in "Protective Groups In Organic Synthesis, Second Edition by T. W. Greene and P. G. M. Wuts, John Wiley&Sons, Inc."

Examples of the protective group of a hydroxyl group include, but are not particularly limited to, a methoxymethyl group, a methylthiomethyl group, a tetrahydrofuranyl group, a 1-ethoxyethyl group, a tert-butyldimethylsilyl group, a benzyl group, a tert-butyl group, an allyl group, and a triphenylmethyl group.

The protective group of a carboxyl group may be the protective group as described with respect to $R_{30}$ and $R_{40}$ above. Examples thereof include, but are not particularly limited to, a methyl group, an ethyl group, a 2,2,2-trichloroethyl group, an ethoxycarbonyl group, a methoxycarbonyl group, a benzyl group, an o-nitrobenzyl group, a p-nitrobenzyl group, a b-p-toluenesulfonylethyl group, a p-methoxybenzyl group, and benzyloxycarbonyl.

Examples of the protective group of a carbonyl group include, but are not particularly limited to, a 1,3-dioxanyl group, a 5-methylene-1,3-dioxanyl group, and a 5,5-dibromo-1,3-dioxanyl group.

Examples of the protective group of an amino group include, but are not particularly limited to, an N-formyl group, an N-acetyl group, an N-chloroacetyl group, an N-benzoyl group, a tert-butyl group, an N-phthalimide group, a diphenylmethyl group, and a benzyl group. One or two of the above protective groups can be appropriately introduced to the amino group.

The leaving group is not particularly limited as long as it is a group that forms a C—N bond as it leaves, examples thereof include a halogen atom such as a fluorine atom, a chlorine atom, and a bromine atom, a trifluoroacetyl group, a methanesulfonyl group, a trifluoromethanesulfonyl group, a p-toluenesulfonyl group, and a diphenoxyphosphoryl group. Among them, a chlorine atom, a bromine atom, and a methanesulfonyl group are preferable.

The compound represented by the formula (II) is producible in accordance with the following scheme (III).

Scheme (III):

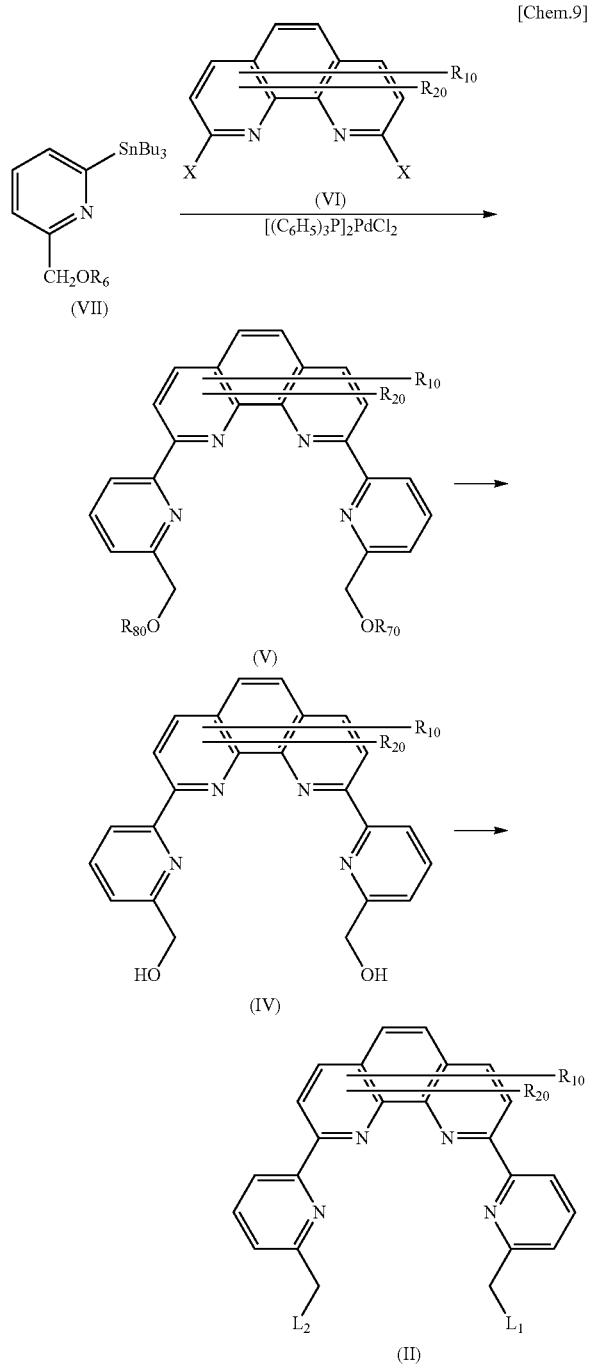

$R_{10}$ and $R_{20}$ as well as $L_1$ and $L_2$ in the scheme (III) represent the same groups as described above, and X represents a halogen atom.

Each of $R_6$, $R_{70}$, and $R_{80}$ independently represents a protective group of a hydroxyl group. $R_{70}$ and $R_{80}$ are the same as or different from each other and each independently represents a protective group of a hydroxyl group. Further, because $R_{70}$ and $R_{80}$ are derived from $R_6$ of the compound represented by the formula (VII), both of $R_{70}$ and $R_{80}$ may be the same as $R_6$.

The present invention also relates to a compound having a phenanthroline structure represented by the following formula (I') or a salt thereof:

Formula (I'):

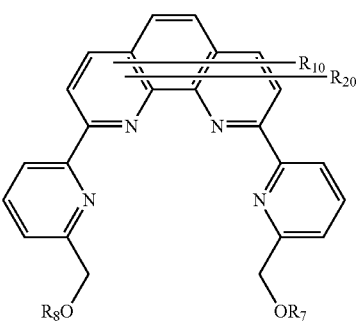

wherein, $R_{10}$ and $R_{20}$ are the same as or different from each other and each independently represents (1) a hydrogen atom, (2) a halogen atom, (3) a hydroxyl group, (4) a cyano group, (5) a nitro group, (6) an amino group, (7) a $C_{1-6}$ alkyl group, (8) a $C_{3-8}$ cycloalkyl group, (9) a $C_{2-6}$ alkenyl group, (10) a $C_{2-6}$ alkynyl group, (11) a $C_{1-6}$ alkoxy group, (12) a $C_{3-8}$ cycloalkoxy group, (13) a $C_{2-6}$ alkenyloxy group, (14) a $C_{2-6}$ alkynyloxy group, (15) a $C_{1-6}$ alkylthio group, (16) a $C_{3-8}$ cycloalkylthio group, (17) a $C_{2-6}$ alkenylthio group, (18) a $C_{2-6}$ alkynylthio group, (19) a $C_{1-6}$ alkylcarbonyloxy group, (20) a formyl group, (21) a $C_{1-6}$ alkylcarbonyl group, (22) a $C_{1-6}$ alkylamino group, (23) a di-$C_{1-6}$ alkylamino group, (24) a $C_{1-6}$ alkylsulfinyl group, (25) a $C_{1-6}$ alkylsulfonyl group, (26) a $C_{3-8}$ cycloalkylsulfinyl group, (27) a $C_{3-8}$ cycloalkylsulfonyl group, (28) a carboxyl group, (29) a $C_{1-6}$ alkyloxycarbonyl group, (30) a $C_{6-14}$ aryl group, or (31) a $C_{7-20}$ aralkyl group, or a group that can be converted to the group (1) to (31).

$R_7$ and $R_8$ are the same as or different from each other and each independently represents a hydrogen atom or a protective group.

$R_7$ and $R_8$ may be groups derived from $R_{70}$ and $R_{80}$ of the compound represented by the formula (V), and the compound represented by the formula (I') encompasses the compound represented by the formula (V) and the compound represented by the formula (IV).

The compound represented by the formula (II) is producible by subjecting the compound represented by the formula (VII) and the compound represented by the formula (VI) to a coupling reaction in the presence of triphenylphosphine palladium dichloride to produce the compound represented by the formula (V), and removing a protective group of a hydroxyl group of the compound represented by the formula (V), and subsequently converting the hydroxyl group to a leaving group.

Reactions of the compound represented by the formula (VII) and the compound represented by the formula (VI) can be carried out in an inert solvent in the presence of triphenylphosphine palladium dichloride.

The compound represented by the formula (VII) is preferably used in an amount of one to five equivalents, more preferable one to three equivalents relative to the compound represented by the formula (VI).

The solvent used in the reaction is not particularly limited as long as it allows the reaction of the compound represented by the formula (VII) and the compound represented by the formula (VI) to smoothly proceed, but examples thereof include dimethylformamide, benzene, toluene, and ethylene chloride. Among them, dimethylformamide is preferable.

Generally, the reaction is preferably carried out in non-aqueous conditions. The reaction is carried out preferably at from room temperature to the boiling point of the solvent, more preferably while heating under reflux. The reaction is completed in 1 hour to 3 to 5 days.

Reactions to remove the protective group of a hydroxyl group of the compound represented by the formula (V) can be carried out in an inert solvent in the presence of an acid.

Examples of the inert solvent used in the reaction include, but is not particularly limited to, alcohols such as methanol, ethyl methyl ketone, acetonitrile, acetone, dimethylformamide, and dimethylacetamide. Among them, methanol is preferable.

The acid is preferably used in an amount of one to five equivalents, more preferable one to three equivalents relative to the compound represented by the formula (V).

Generally, the reaction is carried out preferably at from room temperature to the boiling point of the solvent, more preferably while heating. The reaction is completed in 1 to 24 hours.

The compound represented by the formula (VI) is producible by producing phenanthroline by the methods described in literatures such as:

(1) Dictionary of Organic Compounds, 6$^{th}$ edition, Vol. 5, published by Chapman and Hall, London, UK, 1996, 5167-5168; and (2) Dai yuki kagaku, Vol. 16, Fukusokanshiki kagobutu (Heterocyclic Compound) III, Asakura Publishing Co., Ltd., April 1964, supervised by Munio KOTAKE, 356-363 (Terms in the parentheses are literal translation), and then halogenating the 1- and 9-positions of a phenanthroline ring by the methods described in literatures such as J. C. S. Perkin I, 976-978, 1974.

The compound represented by the formula (VII) is producible by a conventionally known method in accordance with the following scheme (IV), using (6-halopyridine-2-yl) methanol as a starting material.

Scheme (IV):

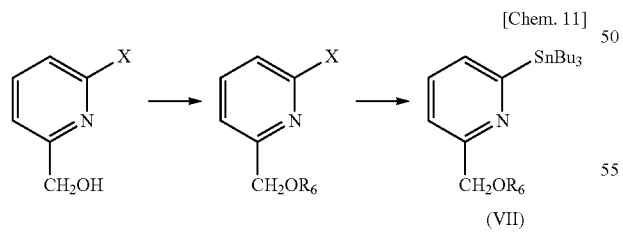

[Chem. 11]

(VII)

In the scheme (IV), X represents a halogen atom, and $R_6$ represents a protective group of a hydroxyl group.

A method for converting a hydroxyl group of the compound represented by the formula (IV) to a leaving group can be carried out by an ordinary method. For example, the method can be carried out by reacting a halide such as thionyl halide such as thionyl chloride and thionyl bromide and a sulfonic acid halide such as p-toluenesulfonyl chloride and p-toluenesulfonyl bromide with the compound represented by the formula (IV) in the presence of a base. The halide to be employed in the reaction is preferably used in an amount of one to five equivalents, more preferable one to three equivalents relative to the compound represented by the formula (IV).

The solvent used in the reaction is not particularly limited as long as it allows the reaction of the compound represented by the formula (IV) and the halide to smoothly proceed, but examples thereof include methylene chloride, chloroform, ethyl methyl ketone, acetonitrile, acetone, dimethylformamide, and dimethylacetamide. Among them, methylene chloride, ethyl methyl ketone, acetonitrile, and acetone are preferable, among which methylene chloride is more preferable.

Examples of the base to be used in the reaction include an alkali metal carbonate salt such as sodium carbonate and potassium carbonate, an alkaline earth metal carbonate salt such as calcium carbonate and magnesium carbonate, and organic alkylamine such as dimethylamine, diethylamine, and triethylamine. Among them, sodium carbonate, potassium carbonate, magnesium carbonate, triethylamine, and the like are preferable, among which triethylamine is more preferable.

The base is preferably used in an amount of one to 10 equivalents, more preferable one to five equivalents relative to the halide. Generally, the reaction is preferably carried out in nonaqueous conditions. The reaction is carried out preferably at from room temperature to the boiling point of the solvent, more preferably while heating under reflux. The reaction is completed in 10 hours to 5 days.

The compound represented by the formula (III) is producible by a conventionally known method in accordance with the following scheme (V).

Scheme (V):

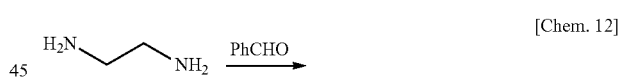

[Chem. 12]

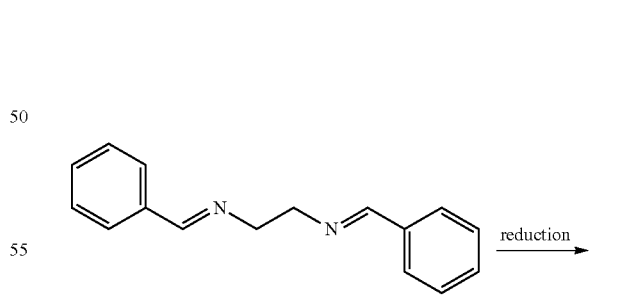

reduction

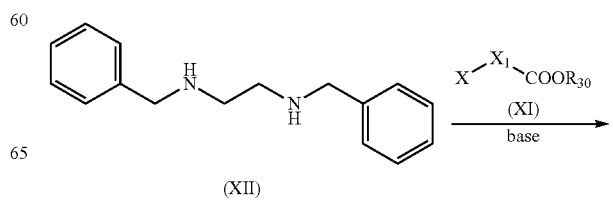

(XII)

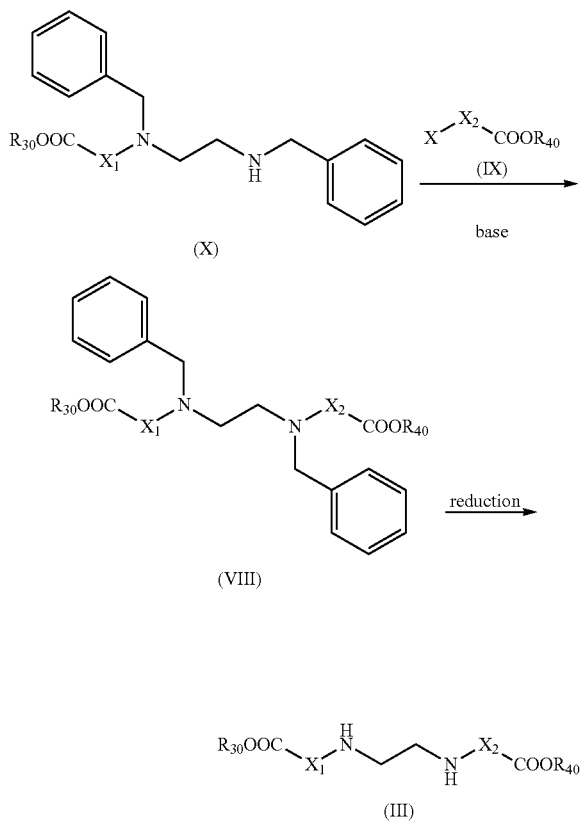

$R_{30}$ and $R_{40}$ as well as $X_1$ and $X_2$ in the scheme (V) represent the same groups as described above, and X represents a halogen atom.

The compound represented by the formula (III) is producible by alkylating the compound represented by the formula (XII) obtainable from ethylenediamine sequentially with the compound represented by the formula (XI) and the compound represented by the formula (IX) to produce the compound represented by the formula (VIII), and then removing an N-benzyl protective group of an amino group of the compound represented by the formula (VIII).

Reactions of the compound represented by the formula (XII) and the compound represented by the formula (XI) can be carried out in an inert solvent in the presence of a base.

The compound represented by the formula (XI) is used in an amount of one to five equivalents, preferably one to three equivalents relative to the compound represented by the formula (XII).

The solvent used in the reaction is not particularly limited as long as it allows the reaction of the compound represented by the formula (XII) and the compound represented by the formula (XI) to smoothly proceed, but examples thereof include acetonitrile, dimethylformamide, benzene, toluene, and methylene chloride. Among them, acetonitrile is preferable.

Generally, the reaction is preferably carried out in nonaqueous conditions. The reaction is carried out preferably at from room temperature to the boiling point of the solvent, more preferably while heating under reflux. The reaction is completed in 1 hour to 3 to 5 days.

Reactions of the compound represented by the formula (X), which is obtainable by reactions of the compound represented by the formula (XII) and the compound represented by the formula (XI), and the compound represented by the formula (IX) can be carried out in a similar manner to the reactions of the compound represented by the formula (XII) and the compound represented by the formula (XI).

Reactions for removing an N-benzyl protective group of an amino group of the compound represented by the formula (VIII) can be carried out by a conventionally known hydrogen-reduction reaction.

The compound represented by the formula (I) can be preferably used as a ligand forming a complex with a metal atom.

In the present invention, formation of a complex by the compound represented by the formula (I) can be confirmed by measuring the fluorescence absorbance of the compound represented by the formula (I) in an aqueous solution containing metal atoms.

Further, in order to utilize a metal complex, for example, as a fluorescent labeling agent for the measurement of biological molecules such as proteins and nucleic acids, not only the metal complex has to be soluble in an organic solvent but also the ligand of the complex per se desirably has hydrophilicity. The compound represented by the formula (I) has better solubility than that of an existing compound utilizable as a ligand in an organic solvent, and it can be provided as a compound with high stability.

Abbreviations used in the present invention have the meanings of the abbreviations commonly used in the art.

EXAMPLES

Hereinafter, the present invention will be described in detail with Examples. However, the present invention will not be limited to these Examples.

Proton nuclear magnetic resonance spectra ($^1$H-NMR) were measured by INOVA500 Spectrometer (500 MHz) manufactured by Varian, Inc., and chemical shifts were recorded in units of d (ppm) relative to tetramethylsilane, and coupling constants were recorded in hertz (Hz).

Patterns have the following meanings; s; singlet, d; doublet, d.d; double doublet, t; triplet, m; multiplet, b; broad, and b.s; broad singlet.

High-performance liquid chromatography (HPLC) measurement was performed using LC-2010A HT manufactured by Shimadzu Corporation. The measurement conditions were as follows.

Column: YMC A302 S-5

UV: 254 nm

ESI-MS measurement was performed using LCMS-2010A manufactured by Shimadzu Corporation. As a column, Inertsil ODS-3 was employed.

Thin layer chromatography (TLC) was performed on a pre-coated silica gel plate (60E-254), and the results were visualized using UV light and ethanolic phosphomolybdic acid for detection.

Example (2.9-bis(6-((Methoxymethyloxy)methyl)pyridine-2-yl)-1,10-phenanthroline) (20)

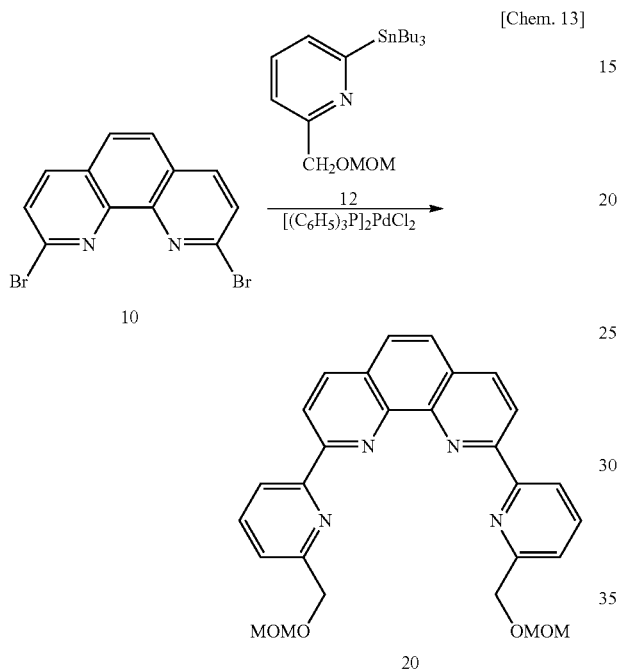

[Chem. 13]

Under a stream of argon, 2,9-dibromo-1,10-phenanthroline (compound (10); 3.25 g; 9.6 mmol) was dissolved in anhydrous dimethylformamide (45 mL). To the reaction mixture, 2-methoxymethyloxymethylpyridine-6-yl tributyltin (compound (12); 17 g; 9.6 mmol) and triphenylphosphine palladium dichloride (3.83 g; 4.8 mmol) were added, followed by stirring at 70° C. for 22 hours. The reaction mixture was cooled to room temperature, and Rochelle salt was added thereto. Subsequently, the reaction mixture was poured into saline, and ethyl acetate was added thereto. Insoluble matters were filtered out, and the filtrate was extracted with ethyl acetate. The organic layer was washed with water and saturated saline, dried over anhydrous sodium sulfate, and then evaporated under reduced pressure to give oil matters. Under a stream of argon, the resulting oil matters were dissolved in anhydrous dimethylformamide (45 mL), and compound (12) (17 g; 9.6 mmol) and triphenylphosphine palladium dichloride (2.72 g; 3.38 mmol) were added thereto, followed by stirring at 70° C. for 20 hours. The reaction mixture was cooled to room temperature, and Rochelle salt was added thereto. Subsequently, the reaction mixture was poured into saline, and ethyl acetate was added thereto. Insoluble matters were filtered out, and the filtrate was extracted with ethyl acetate. The organic layer was washed with water and saturated saline, dried over anhydrous sodium sulfate, and then evaporated under reduced pressure to give a residue. The resulting residue was separated and purified by silica gel column chromatography (SiO$_2$, 200 g; developing solvent: chloroform/methanol=30/1 to 20/1 to 10/1), to give 1.1 g (yield: 23.7%) of the title compound (20).

$^1$H NMR (DMSO-d$_6$) d: 3.38 (s, 3 H), 4.80-4.83 (m, 8 H), 7.64 (d, J=8 Hz, 2 H), 8.07-8.20 (m, 4 H), 8.65-8.84 (m, 4 H), 8.92 (d, J=7 Hz, 1 H)

HPLC mobile phase: 40-95% acetonitrile-water (0.1% trifluoroacetic acid) Peak retention time: 5.7 minutes ESIMS (positive) m/z 483.1, (M+H) (F.W=482.53 for C$_{28}$H$_{26}$N$_4$O$_4$)

2,9-bis(6-(Hydroxymethyl)pyridine-2-yl)-1,10-phenanthroline (21)

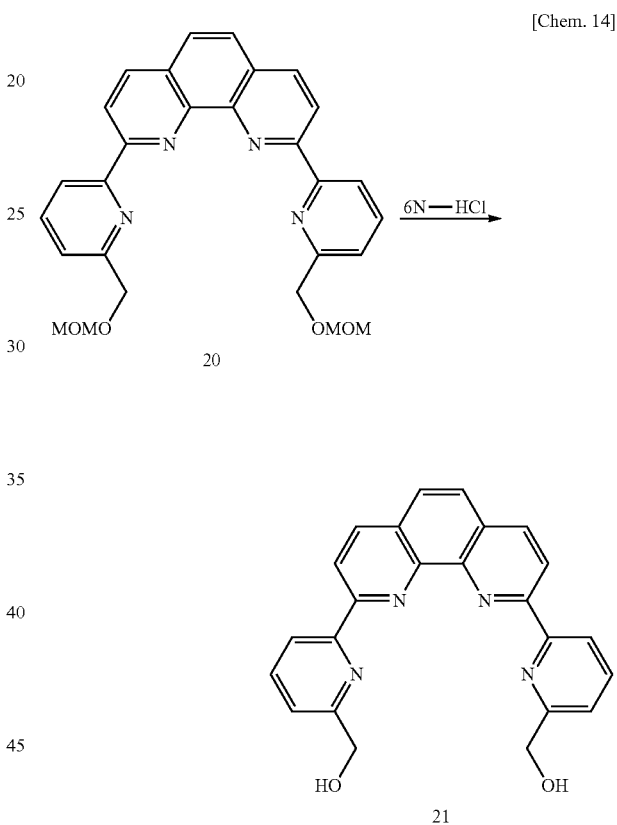

[Chem. 14]

To compound (20) (1.09 g; 2.26 mmol), 6N-hydrochloric acid (5 mL) and methanol (25 mL) were added, and the resulting reaction mixture was stirred at 60° C. for 4 hours. The reaction mixture was evaporated under reduced pressure, and while there was some solvent left the mixture was made alkaline with a 5% aqueous sodium carbonate. Solids which precipitated out were separaetd by filtration. The resulting solids were dissolved in chloroform/methanol=3/1, insoluble matters were filtered out and the filtrate was evaporated under reduced pressure to give 0.72 g (yield: 81%) of the title compound (21).

$^1$H NMR (DMSO-d$_6$) d: 4.76 (d, J=5.5 Hz, 1 H), 5.58 (t, J=6 Hz, 2 H), 7.65 (d, J=7.5 Hz, 2 H), 8.08 (s, 2 H), 8.15 (t, J=7.5 Hz, 2 H), 8.65 (d, J=8.5 Hz, 2 H), 8.84 (d, J=8.5 Hz, 2 H), 8.87 (d, J=8.5 Hz, 2 H)

HPLC mobile phase: 30-80% acetonitrile-water (0.1% trifluoroacetic acid) Peak retention time: 2.7 minutes ESIMS (positive) m/z 395.1, (M+H) (F.W=394.43 for $C_{24}H_{18}N_4O_2$)

2.9-bis(6-(Chloromethyl)pyridine-2-yl)-1,10-phenanthroline (22)

[Chem. 15]

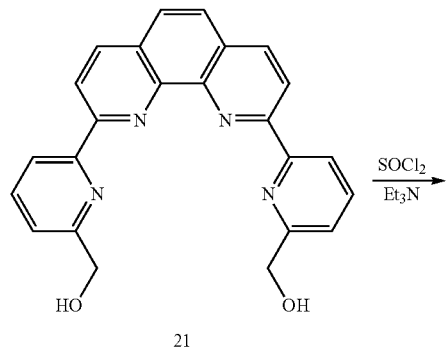

Under a stream of argon, compound (21) (0.7 g; 1.77 mmol) was suspended in methylene chloride (15 mL) in an ice bath. To the reaction mixture, triethylamine (0.54 g; 5.32 mmol) and thionyl chloride (0.51 g; 4.25 mmol) were sequentially added. The resulting reaction mixture was stirred at room temperature for 24 hours. The reaction mixture was made alkaline with a 5% aqueous sodium carbonate, and then evaporated under reduced pressure. The resulting residue was dissolved in chloroform/methanol=3/1, and inorganic matters were removed by membrane filtration. The filtrate was evaporated under reduced pressure to give a residue, and the resulting residue was separated and purified by silica gel column chromatography ($SiO_2$, 200 g) (chloroform/methanol=10/1 to 5/1 to 3/1) to give 0.49 g (yield: 64%) of the title compound (22).

$^1$H NMR (DMSO-$d_6$) d: 4.98 (s, 4 H), 7.74 (d, J=7.5 Hz, 2 H), 8.11 (s, 2 H), 8.20 (t, J=7.5 Hz, 2 H), 8.69 (t, J=8.5 Hz, 2 H), 8.84 (t, J=8 Hz, 2 H), 8.97 (d, J=8.5 Hz, 2 H)

HPLC mobile phase: 30-80% acetonitrile-water (0.1% trifluoroacetic acid) Peak retention time: 8.8 minutes ESIMS (positive) m/z 432.09, (M+H) (F.W=431.32 for $C_{24}H_{15}C_{12}N_4$)

2.5-bis-tert-Butyloxycarbonylmethyl-2,5-diazol-[6]-(5',5')-cyclo-2.9-di-(2'-pyridyl)-1,10-phenanthrolinophane (23)

[Chem. 16]

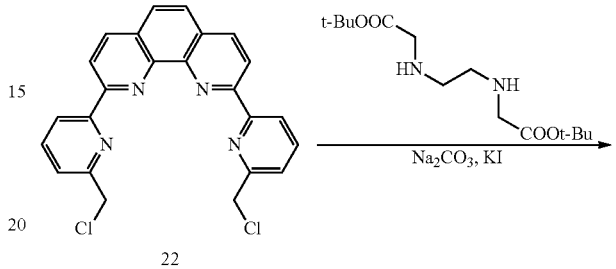

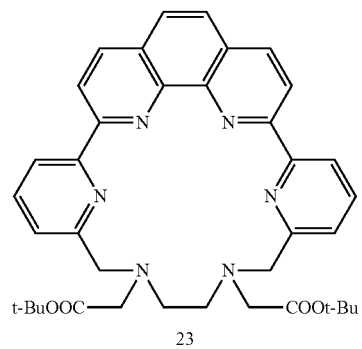

Under a stream of argon, compound (22) (0.71 g; 1.64 mmol) was dissolved in ethylmethylketone (100 mL). To the reaction mixture, N,N'-di-tert-butyloxycarbonylmethyl-1,2-ethylenediamine (0.81g; 4.92 mmol), potassium iodide (0.82 g; 4.92 mmol), and sodium carbonate (0.87 g; 8.2 mmol) were added. The resulting reaction mixture was stirred and refluxed at 110° C. for 44 hours. The reaction mixture was cooled to room temperature and then insoluble matters were filtered out. The filtrate was evaporated under reduced pressure to give a residue, and the resulting residue was separated and purified by silica gel column chromatography ($SiO_2$, 200 g) (chloroform/methanol=20/1 to 10/1) to give 1.04 g (yield: 80%) of the title compound (2).

$^1$H NMR ($CDCl_3$) d: 1.53 (s, 18 H), 2.91 (b.s, 4 H), 3.52 (b.s, 4 H), 4.10 (b.s, 4 H), 7.34 (d, J=7.5 Hz, 2 H), 7.57 (s, 2 H), 7.61 (t, J=7.5 Hz, 2 H), 8.17 (d, J=8.5 Hz, 2 H), 8.74 (d, J=8.5 Hz, 2 H), 8.80 (d, J=8.5 Hz, 2 H)

HPLC mobile phase: 40-95% acetonitrile-water (0.1% trifluoroacetic acid) Peak retention time: 12.2 minutes ESIMS (positive) m/z 647.1, (M+H) (F.W=646.78 for $C_{38}H_{42}N_6O_4$)

2,5-bis-Carboxymethyl-2,5-diazo[6]-(5',5')-cyclo-2,9-di-(2'-pyridyl)-1,10-phenanthrolinophane (24)

[Chem. 17]

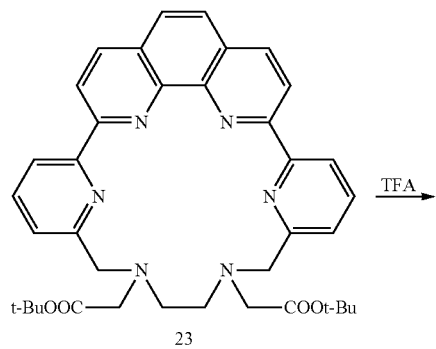

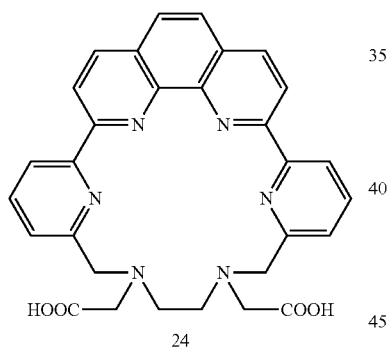

Under a stream of argon, 0.44 g of compound (23) was dissolved in methylene chloride (3.5 mL). To the reaction mixture, anisole (0.4 mL) and trifluoroacetic acid (1.5 mL) were added at room temperature. The resulting reaction mixture was stirred at room temperature for 19 hours. The reaction mixture was evaporated under reduced pressure and to the resulting residue was added 1N hydrochloric acid, and then the reaction mixture was evaporated under reduced pressure. Subsequently, using HP-20SS (30 mL), the resulting residue was eluted in an eluting solution of 10%, 20%=acetonitrile/water, and the fractions were collected and freeze-dried to give 150 mg of the title compound (24).

$^1$H NMR (DMSO-d$_6$) d: 3.04 (s, 4 H), 3.61 (s, 4 H), 4.08 (s, 4 H), 7.23 (d, J=7.5 Hz, 2 H), 7.47 (s, 2 H), 7.66 (t, J=7.5 Hz, 2 H), 8.09 (d, J=8.5 Hz, 2 H), 8.35 (d, J=8.5 Hz, 2 H), 8.46 (d, J=7.5 Hz, 2 H)

HPLC mobile phase: 20-90% acetonitrile-water (0.1% trifluoroacetic acid) Peak retention time: 5.3 minutes ESIMS (positive) m/z 535 (M+H) (F.W=534.57 for $C_{30}H_{26}N_6O_4$)

Reference Example 1

1-Methyl-1,10-phenanthrolinium iodide (1)

[Chem. 18]

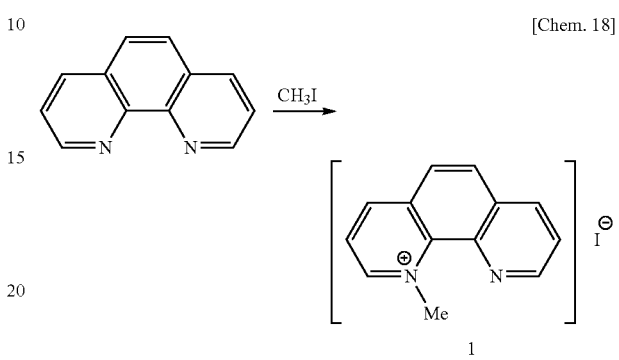

Under a stream of argon, 1,10-phenanthroline (23 g; 127 mmol) was dissolved in nitrobenzene (500 mL). To the reaction mixture, methyl iodide (45.29 g; 319 mmol) was added dropwise at 35° C. over 3.5 hours. The resulting reaction mixture was stirred at 35° C. for 24 hours. The reaction mixture was cooled in an ice bath, filtered out. The resulting solids were sequentially washed with nitrobenzene, benzene, and ethanol, and evaporated under reduced pressure to give 36 g (yield: 88%) of the title compound (1).

$^1$H NMR (DMSO-d$_6$) d: 5.29 (s, 3 H), 8.07 (d, d, J1=8 Hz, J2=4.5 Hz, 1 H), 8.43 (d, J=2.5 Hz, 1 H), 8.43 (q, J=9Hz, 2 H), 8.81 (d, d, J1=8.5 Hz, J2=1.5 Hz, 1 H), 9.32-9.60 (m, 3H)

Reference Example 2

1-Methyl-1,10-phenanthroline-2(1H)-one (2)

[Chem. 19]

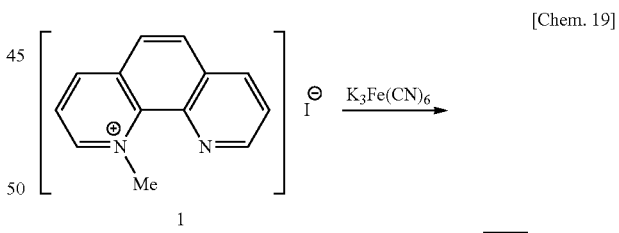

To a stirred aqueous solution of potassium ferricyanide (92.2 g; 280 mmol) (1.12L), compound (1) (37.6 g; 117 mmol) and an aqueous solution of sodium hydroxide (69.3 g; 1.73 mol) (200 mL) were alternately added in an ice bath (inner temperature of 10 to 15° C.) over 20 minutes. The resulting reaction mixture was stirred at room temperature for 3 hours. Crude crystals which precipitated out were filtered out and dried. The resulting crude crystals were dissolved in toluene (1.1 L) and benzene (450 mL), and insoluble matters were filtrated out. The filtrate was evaporated under reduced pressure, and the resulting residue was washed with isopropyl ether and ethyl acetate, and then dried to give 23.7 g (yield: 75%) of the title compound (2).

$^1$H NMR (DMSO-$d_6$) d: 4.22 (s, 3 H), 6.84 (d, J=9 Hz, 1 H), 7.69 (d, d, J1=8 Hz, J2=2 Hz, 1 H), 7.77 (d, J=8 Hz, 1 H), 7.82 (d, J=8.5 Hz, 1 H), 8.08 (d, J=9.5 Hz, 1 H), 8.46 (d, d, J1=8 Hz, J2=2 Hz, 1 H), 9.0 (d, d, J1=9.5 Hz, J2=2 Hz, 1 H)

Reference Example 3

2-Chloro-1.10-phenanthroline (3)

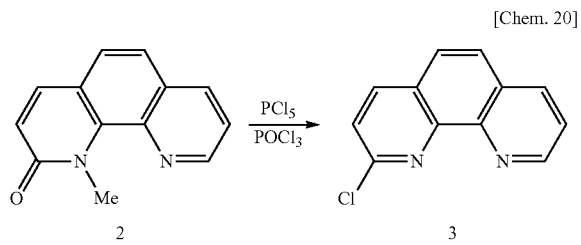

Under a stream of argon, to compound (2) (8 g; 38 mmol), phosphorus oxychloride (72 mL) and phosphorus pentachloride (9.8 g; 47.6 mmol) were added in an ice bath. The resulting reaction mixture was stirred and refluxed for 8 hours, and excess phosphorus oxychloride was removed under reduced pressure. To the resulting reaction concentrate, ice water and concentrated aqueous ammonia were added and the resulting mixture was made alkaline to precipitate crude crystals. The crude crystals were separated by filtration and washed with water, and then dried under reduced pressure to give 6.1 g (yield: 75%) of the title compound (3).

$^1$H NMR (DMSO-$d_6$) d: 7.80-7.88 (m, 2 H), 8.07 (s, 2 H), 8.54 (d, J=8.5 Hz, 1 H), 8.60 (d, J=8.5 Hz, 1H), 9.14 (d, J=7 Hz, 1H)

Reference Example 4

9-Chloro-1-methyl-1,10-phenanthrolinium hydrogen sulfate (4)

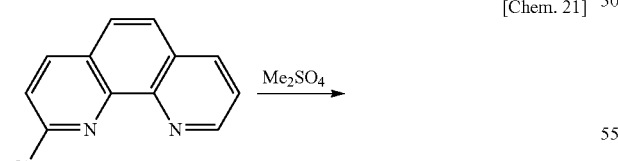

Under a stream of argon, to compound (3) (5.2 g; 24.2 mmol), dimethyl sulfate (22.1 g; 175 mmol) was added at room temperature over 10 minutes. The reaction temperature was raised to 120° C. and the resulting reaction mixture was stirred for 1 hour and then cooled to room temperature. Diethyl ether was added thereto and light brown crude crystals which precipitated out were separated by filtration. The obtained crude crystals were washed with a solution of diethyl ether/ethanol=1/1 to 1/2 and dried under reduced pressure to give 6.17 g of the title compound (4).

$^1$H NMR (DMSO-$d_6$) d: 5.12 (s, 3 H), 8.18 (d, J=8.5 Hz, 1 H), 8.40-8.50 (m 3 H), 8.88 (d, J=9 Hz, 1 H), 9.42 (d, J=9 Hz, 1 H), 9.60 (d, J=7 Hz, 1H)

Reference Example 5

9-Chloro-1-methyl-1.10-phenanthroline-2(1H)-one (5)

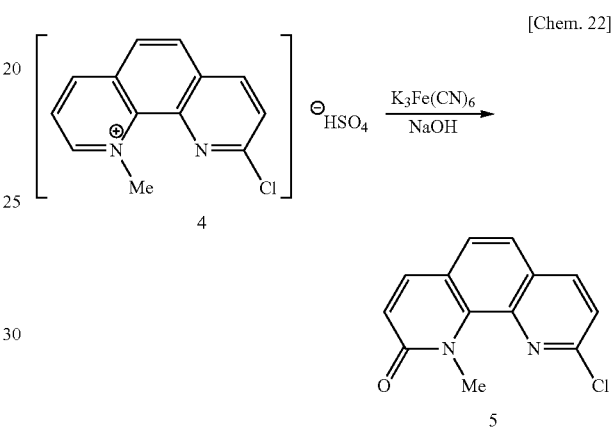

To a stirred aqueous solution of potassium ferricyanide (22.1 g; 673 mmol) (200 mL) in an ice bath, compound (4) (6.17 g; 26.9 mmol) and an aqueous sodium hydroxide (16.14 g; 404 mmol) (110 mL) were alternately added over 20 minutes. The resulting reaction mixture was stirred in an ice bath, and further stirred at room temperature for 3.5 hours. Crude crystals which precipitated out were separated by filtration and dried, and then dissolved in methanol, and subsequently subjected to an activated carbon treatment. Then, a filtrate was concentrated under reduced pressure to give 4.26 g (yield: 72% from compound (3)) of the title compound (5).

$^1$H NMR (DMSO-$d_6$) d: 4.35 (s, 3 H), 6.87 (d, J=9 Hz, 1 H), 7.76 (d, J=8.5 Hz, 1 H), 7.83 (d, J=8.5 Hz, 1 H), 7.89 (d, J=8.5 Hz, 1 H), 8.09 (d, J=9 Hz, 1 H), 8.54 (d, J=9 Hz, 1 H)

Reference Example 6

2,9-Dichloro-1,10-phenanthroline (6)

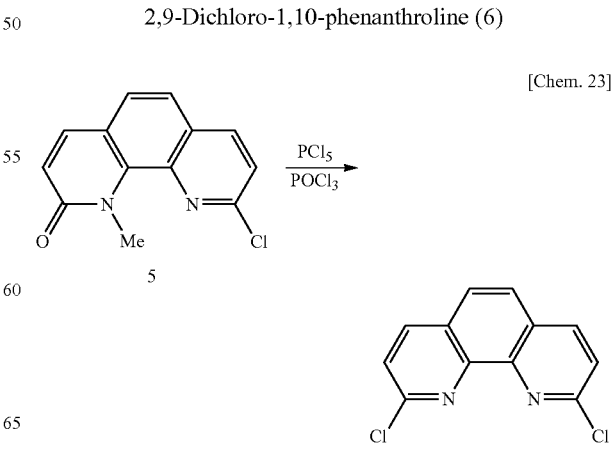

Under a stream of argon, to compound (5) (4.26 g; 17.4 mmol), phosphorus oxychloride (39 mL) and phosphorus pentachloride (4.48 g; 21.8 mmol) were added in an ice bath. The resulting reaction mixture was stirred and refluxed for 7 hours, and then evaporated under reduced pressure to remove phosphorus oxychloride. To the resulting residue, ice water and concentrated aqueous ammonia were added and the resulting reaction mixture was made alkaline. The solids which precipitated out were separated by filtration and washed with water, and then dried under reduced pressure to give 4.06 g (yield: 94%) of the title compound (6).

$^1$H NMR (DMSO-$d_6$) d: 7.90 (d, J=8.5 Hz, 1 H), 8.12 (s, 2 H), 8.63 (d, J=8.5 Hz, 1 H)

HPLC mobile phase: 20-90% acetonitrile-water (0.1% trifluoroacetic acid) Peak retention time: 13.2 minutes Reference Example 7

2-Bromo-1,10-phenanthroline (7)

[Chem. 24]

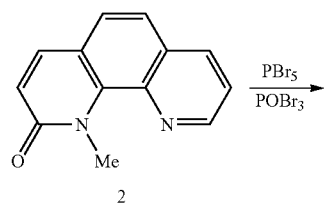

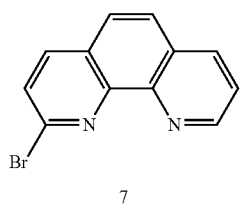

Under a stream of argon, to compound (2) (10 g; 47.6 mmol), phosphorus pentabromide (28 g; 65 mmol) and phosphorus oxybromide (50 g; 174 mmol) were added at room temperature. The reaction temperature was raised to 80° C. and the reaction mixture was stirred for 6 hours. The reaction mixture was cooled in an ice bath, and then poured into ice water. Concentrated aqueous ammonia was added thereto and the resulting mixture was made alkaline. The reaction mixture was extracted with chloroform, and the organic layer thus obtained was washed with water, dried over sodium sulfate, and then evaporated under reduced pressure. The resulting residue was separated and purified by silica gel column chromatography (SiO$_2$, 250 g) (toluene/ethyl acetate=5/1 to 3/1 to 1/1 to ethyl acetate), to give 6.9 g (yield: 94%) of the title compound (7).

$^1$H NMR (CDCl$_3$) d: 7.66 (d, d, J1=8 Hz, J2=4.5 Hz, 1 H), 7.76-7.79 (m, 2 H), 7.83 (d, J=8.5 Hz, 1 H), 8.08 (d, J=8.5 Hz, 1 H), 8.26 (d, d, J1=8 Hz, J2=2 Hz, 1 H), 9.24 (d, J1=4.5 Hz, J2=2 Hz, 1H)

HPLC mobile phase: 20-90% acetonitrile-water (0.1% trifluoroacetic acid) Peak retention time: 4.2 minutes ESIMS (positive) m/z 260.9, 258.2 (M+H) (F.W=259.1 for C$_{12}$H$_7$BrN$_2$)

Reference Example 8

9-Bromo-1-methyl-1,10-phenanthrolinium hydrogen sulfate (8)

[Chem. 25]

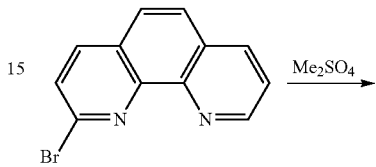

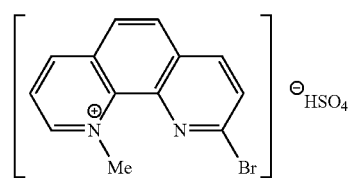

Under a stream of argon, to compound (7) (24.4 g; 94.2 mmol), dimethyl sulfate (77 g; 610 mmol) was added in an ice bath over 20 minutes. The reaction temperature was raised to 120° C. and the resulting reaction mixture was stirred for 1 hour. To the reaction mixture, diethyl ether was added in an ice bath, and solids which precipitated out were separated by filtration. The resulting solids were washed with a mixed solution of diethyl ether/ethanol (1/1 to 1/2) and dried under reduced pressure to give 33.6 g (yield: 96%) of the title compound (8).

$^1$H NMR (DMSO-$d_6$) d: 5.19 (s, 3 H), 8.29 (d, J=8.5 Hz, 1 H), 8.43-8.50 (m, 3 H), 8.77 (d, J=8.5 Hz, 1 H), 9.44 (d, J=8.5 Hz, 1 H), 9.64 (d, J=6 Hz, 1 H)

HPLC mobile phase: 20-90% acetonitrile-water (0.1% trifluoroacetic acid) Peak retention time: 5.2 minutes ESIMS (positive) m/z 274.9, 272.9 (M+H) (F.W=274.14 for C$_{13}$H$_{10}$BrN$_2$)

Reference Example 9

9-Bromo-1-methyl-1,10-phenanthroline-2(1H)-one (9)

[Chem. 26]

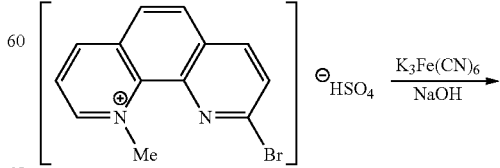

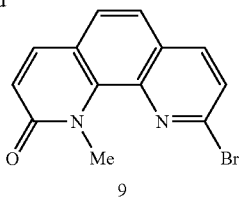

9

To a stirred aqueous solution of potassium ferricyanide (100 g; 303 mmol) (1.1 L), compound (8) (42.7 g; 115 mmol) and an aqueous sodium hydroxide (76 g; 1.9 mol) (110 mL) were alternately added over 25 minutes in an ice bath (inner temperature of 4 to 6° C.). The resulting mixture was stirred in an ice bath for 1 hour, and further stirred at room temperature for 3.5 hours. Crude crystals which precipitated out were separated by filtration and washed with water, and then dried. The resulting crude crystals were separated and purified by silica gel column chromatography ($SiO_2$ 800 g) (chloroform/methanol=50/1 to 30/1 to 20/1) and dried to give 27.4 g (yield: 82%) of the title compound (9).

$^1$H NMR ($CDCl_3$) d: 4.39 (s, 3 H), 6.92 (d, J=9.5 Hz, 1 H), 7.54 (d, J=8.5 Hz, 1 H), 7.60 (d, J=8.5 Hz, 1 H), 7.61 (d, J=8.5 Hz, 1 H), 7.77 (d, J=9.5 Hz, 1 H), 8.01 (d, J=8.5 Hz, 1 H)

HPLC mobile phase: 20-90% acetonitrile-water (0.1% trifluoroacetic acid) Peak retention time: 14.2 minutes ESIMS (positive) m/z 290.9, 288.2 (M+H) (F.W=289.13 for $C_{13}H_9BrN_2O$)

Reference Example 10

2,9-Dibromo-1,10-phenanthroline (10)

[Chem. 27]

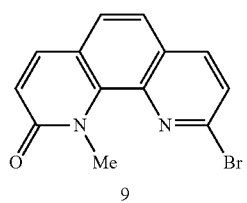  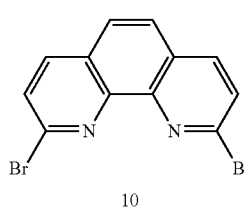

Under a stream of argon, to compound (9) (8.4 g; 29.1 mmol), phosphorus oxybromide (3.25 g; 174 mmol) and phosphorus pentachloride (15.4 g; 35.8 mmol) were added in an ice bath. The reaction temperature was raised to 65 to 75° C., and the resulting reaction mixture was stirred for 5.5 hours. The reaction mixture was cooled in an ice bath and evaporated under reduced pressure. Excess phosphorus oxybromide was removed and the resulting reaction concentrate was poured into ice water, and was made alkaline with concentrated aqueous ammonia. While solids which precipitated out were separated by filtration, they were washed with water to give crude title compound (10). The crude compound (10) was dried, and separated and purified by silica gel column chromatography ($SiO_2$ 300 g) ($CHCl_3$/methanol=50/1 to 40/1 to 30/1) to give 8 g (yield: 81%) of the title compound (10).

$^1$H NMR ($CDCl_3$) d: 8.02 (d, J=8.5 Hz, 2 H), 8.12 (s, 2 H), 8.51 (d, J=8.5 Hz, 2 H)

HPLC mobile phase: 20-90% acetonitrile-water (0.1% trifluoroacetic acid) Peak retention time: 16 minutes ESIMS (positive) m/z 340.8, 338.8, 336.8 (M+H) (F.W=338.00 for $C_{12}H_6Br_2N_2$)

Reference Example 11

2-Bromo-6-((methoxymethyloxy)methyl)pyridine (11)

[Chem. 28]

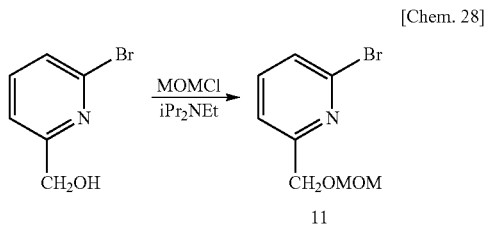

Under a stream of argon, (6-bromopyridine-2-yl)methanol (10 g; 53.2 mmol) was dissolved in methylene chloride (50 mL). Diisopropylethylamine (9.6 g; 74.5 mmol) and chloromethyl methyl ether (5.35 g; 66.5 mmol) were added to the reaction mixture in an ice bath, and further, the reaction mixture was stirred at room temperature for 17 hours. The reaction solution was poured into ice water and extracted with chloroform. The organic layer was washed with water, dried over sodium sulfate, and then evaporated under reduced pressure. The resulting residue was separated and purified by silica gel column chromatography ($SiO_2$, 200 g) (toluene/ethyl acetate=10/1) to give 12.15 g (yield: 98%) of the title compound (11).

$^1$H NMR ($CDCl_3$) d: 3.42 (s, 3 H), 4.69 (s, 2 H), 4.77 (s, 2 H), 7.38-7.44 (m, 2 H), 7.56 (t, J=7.5 Hz, 1 H)

Reference Example 12

2-((Methoxymethyloxy)methyl)-6-(tributylstannyl)pyridine (12)

[Chem. 29]

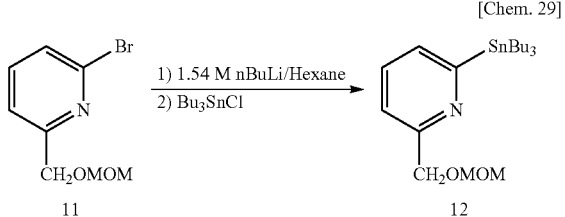

Under a stream of argon, compound (11) (24.7 g; 106 mmol) was dissolved in anhydrous tetrahydrofuran (270 mL), and 1.54M n-butyllithium hexane solution was added dropwise thereto over 50 minutes at −65 to −70° C. The resulting reaction mixture was stirred at −65 to −70° C. for 1 hour. To the reaction mixture, tetrahydrofuran solution of 40 g (122 mmol) of tributyltin chloride (100 mL) was added dropwise over 30 minutes. While gradually raising the temperature of the reaction solution (to −20° C.), the reaction mixture was stirred at −20° C. for 20 hours. To the reaction mixture, water (250 mL) was added, and the resulting mixture was extracted with diethyl ether three times. The organic layer was dried over magnesium sulfate and evaporated under reduced pressure to give 58 g of the crude title compound (12). The obtained compound was used in the next step without further purifying.

Industrial Applicability

The novel compound having a phenanthroline structure of the present invention is useful as a ligand of an analytical marker utilizing fluorescence.

The invention claimed is:

1. A compound having a phenanthroline structure of formula (I) or a salt thereof:

Formula (I):

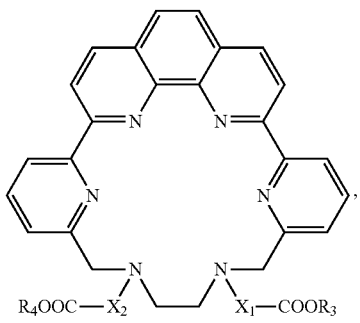

wherein,
$R_3$ and $R_4$ are each independently a hydrogen atom, a $C_{1-6}$ alkyl group, a $C_{3-8}$ cycloalkyl group, a $C_{2-6}$ alkenyl group, a $C_{2-6}$ alkynyl group, a $C_{6-14}$ aryl group, or a $C_{7-20}$ aralkyl group; and $X_1$ and $X_2$ are each independently the following structure:

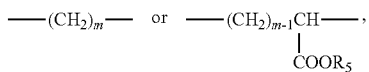

wherein, m is an integer of from 1 to 6; and
$R_5$ is a hydrogen atom, a $C_{1-6}$ alkyl group, a $C_{3-8}$ cycloalkyl group, a $C_{2-6}$ alkenyl group, a $C_{2-6}$ alkynyl group, a $C_{6-14}$ aryl group, or a $C_{7-20}$ aralkyl group.

2. The compound or the salt thereof according to claim 1, wherein each of $R_3$ and $R_4$ are a hydrogen atom.

3. A compound having a phenanthroline structure of formula (I') or a salt thereof:

Formula (I'):

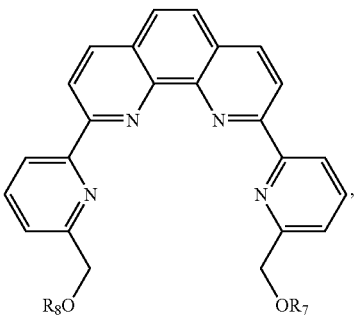

wherein,
$R_7$ and $R_8$ are each independently a hydrogen atom or a protecting group.

* * * * *